United States Patent [19]

Chupp

[11] 4,098,600
[45] Jul. 4, 1978

[54] ISOCYANOACYLAMIDES

[75] Inventor: John P. Chupp, Kirkwood, Mo.

[73] Assignee: Monsanto Company, St. Louis, Mo.

[21] Appl. No.: 778,305

[22] Filed: Mar. 16, 1977

Related U.S. Application Data

[63] Continuation-in-part of Ser. No. 689,214, May 24, 1976, abandoned.

[51] Int. Cl.$^2$ .................. C07C 119/02; A01N 9/20
[52] U.S. Cl. .................................. 71/105; 71/70; 260/465 D
[58] Field of Search .................. 260/465 D; 71/105

[56] References Cited

U.S. PATENT DOCUMENTS

| | | | |
|---|---|---|---|
| 3,116,312 | 12/1963 | Shepherd et al. | 260/465 D |
| 3,636,036 | 1/1972 | Ugi | 260/465 D |
| 3,708,517 | 1/1973 | Ugi | 260/465 D |
| 3,803,208 | 4/1974 | Szabo | 260/465 D |

FOREIGN PATENT DOCUMENTS 2,218,009  11/1973  Fed. Rep. of Germany.

OTHER PUBLICATIONS

Houben–Weyl, Methoden Der Organischen Chemie, Band VIII, (1952), Sauerstaffnerbindgienen–III, pp 351–353.

*Primary Examiner*—Joseph Paul Brust
*Attorney, Agent, or Firm*—Richard H. Shear; Donald W. Peterson

[57] ABSTRACT

Isocyanoacylamides have been found to inhibit the growth of broadleaf plants, especially when applied as a post-emergent. At lower rates, the compounds of the invention are effective in regulating the growth of corn plants.

11 Claims, No Drawings

ISOCYANOACYLAMIDES

This application is a continuation-in-part of Ser. No. 689,214, filed May 24, 1976 now abandoned.

The invention relates to novel compounds and their use in agriculture. More particularly, the invention relates to the use of novel isocyanoacylamides to inhibit the growth of broadleaf weeds as well as regulate the growth of corn plants.

U.S. Pat. Nos. 2,863,752 and 2,864,683 to Hamm and Speziale disclose the use of specific α-haloacetamides as herbicides. In said patents as well as an article entitled "Effect of Variations in the Acyl Moiety on Herbicidal Activity of N-Substituted Alpha-Chloroacetamides", *Agricultural and Food Chemistry*, Vol. 5, No. 1, January 1957, Hamm and Speziale place much emphasis on the criticality of the single halogen substituent on the α-carbon as well as the substitution of the nitrogen atom of the α-haloacetamide herbicides. α-substituents other than the single halogen atom were found to herbicidally inactivate the acetamides. Further, Hamm and Speziale found the α-haloacetamides to be useful in selectively inhibiting the growth of narrowleaf grasses in broadleaf plants when applied as a pre-emergent herbicide.

The compounds of the present invention have been found to be effective in inhibiting the growth of broadleaf weeds as well as regulating the growth of corn plants. Generally, the growth of broadleaf weeds has been found to be inhibited by post-emergent application thereto of isocyanoacylamides of the formula $$\begin{array}{c} R_1 \\ \diagdown \\ \phantom{R_2}N-\overset{\overset{\displaystyle O}{\|}}{C}-CH-N\equiv C \\ \diagup \phantom{N-C-}\big| \\ R_2 \phantom{N-C-}R_3 \end{array} \quad (I)$$

wherein $R_1$ is selected from the group consisting of hydrogen, lower alkyl, phenyl, substituted phenyl, benzyl and disubstituted benzyl; $R_2$ and $R_3$ are independently selected from the group consisting of hydrogen and lower alkyl; provided that $R_2$ is not hydrogen when $R_1$ is phenyl.

If instead of herbicidal activity, regulation of corn plant growth is desired, such regulation may be achieved by application to said corn plant of the novel N-substituted isocyanoacylamides having the formula $$\begin{array}{c} R_1 \\ \diagdown \\ \phantom{R_2}N-\overset{\overset{\displaystyle O}{\|}}{C}-CH_2-N\equiv C \\ \diagup \\ R_2 \end{array} \quad (II)$$

wherein $R_1$ is phenyl, substituted phenyl, benzyl and disubstituted benzyl; $R_2$ is hydrogen and lower alkyl.

By the term "lower alkyl" as used herein is meant those alkyl groups having up to four carbon atoms inclusive. The term "substituted phenyl" as used herein means a phenyl substituent in which a halogen or lower alkyl has been substituted for one or more of the ring hydrogen atoms. The term "disubstituted benzyl" as used herein means a benzyl substituent in which the benzene ring has two halogen or lower alkyl substituents.

Generally, the primary and secondary isocyanoacylamides of the invention may be prepared by reacting the appropriate α-isocyano acid ester with ammonia or the approprite amine in accordance with Scheme A, below.

Scheme A $$CN-CH-\overset{\overset{\displaystyle O}{\|}}{C}-OR_4 + R_1NH_2 \longrightarrow$$
$$\phantom{CN-C}\big|$$
$$\phantom{CN-CH}R_3$$

$$R_4 = \text{alkyl} \qquad CN-CH-\overset{\overset{\displaystyle O}{\|}}{C}-NHR_1$$
$$\phantom{R_4 = \text{alkyl} \quad CN-C}\big|$$
$$\phantom{R_4 = \text{alkyl} \quad CN-CH}R_3$$

The following examples are presented to illustrate the preparation of the compounds of the invention in accordance with Scheme A.

EXAMPLE 1

To a reaction flask containing 3.2 g. of benzylamine was added 3.4 g. of ethyl-α-isocyanoacetate. After standing for 5 hours at room temperature, the contents of the flask had crystallized. The crystals were washed with hexane and filtered. Upon recrystallization from methanol, a white crystalline compound was obtained that melted at 122°–124° C. and was identified as N-benzyl-α-isocyanoacetamide.

EXAMPLE 2

To 1.8 g. of isopropylamine was added 3.4 g. of ethyl-α-isocyanoacetate. After standing overnight at room temperature, 0.9 g. of additional isopropylamine was added. Upon removal of ethanol and amine by vacuum, the solid residue was recrystallized from ether to give a compound that melted at 68°–71° C. identified as N-isopropyl-α-isocyanoacetamide.

EXAMPLES 3–7

Utilizing the procedure of Scheme A and Examples 1 and 2, the following compounds have been prepared.

| Example | Compounds | Melting Point |
|---|---|---|
| 3 | N-(2,6-diethylbenzyl)-2-isocyano-acetamide | 138–140° C. |
| 4 | N-(2,6-dichlorobenzyl)-α-isocyanoacetamide | 174–176° C. |
| 5 | N-(3,4-dichlorobenzyl)-α-isocyanoacetamide | 133–135° C. |
| 6 | N-methyl-α-isocyanoacetamide | 82–84° C. |
| 7 | α-isocyanoacetamide | 119–121° C. |

EXAMPLE 8

To 5.35 g. of benzylamine was added 6.35 g. of ethyl-2-isocyanopropionate. After being allowed to stand overnight, scratching induced crystallization. Recrystallization from ether gave a compound identified as N-benzyl-2-isocyanopropionamide melting at 68°–70° C.

Tertiary amides may be prepared by first preparing the 2-aminoacyl amide either through direct ammonialysis or by Gabriel synthesis from the corresponding 2-chloroacetamide. Formylation is then accomplished either by direct action of concentrated formic acid or a mixed formic-acetic anhydride reagent. The resulting formamide may then be dehydrated with about 1.5 moles of $POCl_3$ per mole of amide. Examples 9 and 10 are provided as illustrations of the preparation of the tertiary amides of the invention.

EXAMPLE 9

α-amino-N-isopropylpropionanilide (88.5 g.) was mixed with 80 g. of concentrated formic acid, then heated at 125° C. for 2 hours. The temperature was lowered to 100° C. and toluene added. The mixture was then refluxed. Water and formic acid were removed azeotropically. Upon crystallization, the toluene solvent was removed and the residue, identified as N-isopropyl-2-formamido propionanilide, triturated with ether and filtered. The formamide, (23.4 g.), was dissolved in methylene chloride and 50.5 g. triethylamine added thereto. The clear solution was cooled to −10° C. and 22.8 g. $POCl_3$ added. After stirring at below zero temperature for 15 minutes, excess 10% sodium carbonate solution was added, taking care that temperature did not exceed 20° C. The mixture was allowed to stir at ambient temperature briefly, then the layers were separated. The organic layer was washed with 100 ml 2% salt solution, dried over $MgSO_4$, filtered and stripped. The oily residue was taken up in methylcyclohexane and stirred. The cyclohexane solution was decanted from the insoluble oil and cooled and scratched to produce a solid which was filtered and air-dried. Recrystallization from heptane provided 2-isocyano-N-isopropyl-propionanilide melting at 47°–50° C.

EXAMPLE 10

α-amino-N-isopropylacetanilide (76.8 g.) was mixed with 97% formic acid, boiling chips added and the mixture refluxed for 2 hours. After cooling to 110° C. and adding toluene, the temperature was again raised to reflux and held for 24 hours. The solvent was then removed and the residue recrystallized from benzene to give α-formamido-N-isopropylacetanilide. To a flask equipped with drying tube was added 55 g. of α-formamido-N-isopropylacetanilide. Triethylamine (126.0 g.) and 400 ml. methylene chloride were then added. The resulting clear solution was cooled to −10° and dropwise addition of $POCl_3$ started (57.5 g.). The temperature was lowered to −10° and continuous addition of sodium carbonate solution (1.0 mole, 106 g.) was commenced, keeping the temperature at 0° or lower. After addition, more water was added and the mixture allowed to stir at room temperature for 30 minutes. The organic layer was separated off, and filtered through $MgSO_4$. The organic layer was then washed with salt water, and again filtered through $MgSO_4$. The material was dried over $MgSO_4$, filtered, and vacuum treated to remove methylene chloride. The residue was recrystallized from ether to give α-isocyano-N-isopropylacetanilide melting at 80°–82° C.

In accordance with the present invention, the isocyanoacylamides of the foregoing formula possess herbicidal properties especially in inhibiting the growth of broadleaf weeds. A preferred herbicidal compound is α-isocyanoacetamide. Note that $R_1$, $R_2$ and $R_3$ are each hydrogen. This is quite surprising in view of the teachings of U.S. Pat. Nos. 2,863,752 and 2,864,683 that $R_1$ and $R_2$ may not both be hydrogen.

The table below summarizes the results of tests conducted to determine the post-emergent herbicidal activity of α-isocyanoacetamide.

The post-emergent tests were conducted as follows. The active ingredients are applied in spray form to 2 or 3-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately 4 weeks later the effects are observed and recorded. The results are shown in Table II in which the post-emergent herbicidal rating code is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the following legend:

| | |
|---|---|
| A - Soybean | I - Hemp Sesbania |
| B - Sugar Beet | J - Lambsquarters |
| C - Wheat | K - Smartweed |
| D - Rice | L - Velvet Leaf |
| E - Sorghum | M - Downy Brome |
| F - Cocklebur | N - Panicum Spp |
| G - Wild Buckwheat | O - Barnyard Grass |
| H - Morning Glory | P - Crabgrass |

| | | Plant Species | | | | | | | | | | | | | | | |
|---|---|---|---|---|---|---|---|---|---|---|---|---|---|---|---|---|---|
| Compound | kg/h | A | B | C | D | E | F | G | H | I | J | K | L | M | N | O | P |
| α-isocyanoacetamide | 4.48 | 1 | 2 | 0 | 0 | 1 | 2 | 0 | 1 | 4 | 4 | 2 | 2 | 0 | 3 | 1 | 3 |
| α-isocyanoacetamide | 1.12 | 0 | 0 | 0 | 0 | 0 | 1 | 0 | 0 | 3 | 3 | 1 | 2 | 0 | 2 | 1 | 3 |

In addition, the compounds of Examples 1, 2 and 4 have been found to be effective in controlling up to 50% of at least one or more of the broadleaf plant species listed above, while up to 75% of at least one or more of said broadleaf plant species has been found to be controlled by the compounds of Examples 3, 5, 6, 8 and 9.

For the sake of brevity and simplicity, the term "active ingredient" has been used herein and is used hereinafter to describe the isocyanoacylamides of the foregoing formula.

As noted previously, the N-substituted isocyanoacylamides of Formula II above have been found to be effective in regulating the growth of corn plants. By the term "regulation of growth of plants" or "plant growth regulation" is meant a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolongated dormancy, increased cold hardiness, delayed or accelerated ripening, thinning of fruit, prevention of pre-harvest fruit drop and the like.

Modifications in the normal sequential development of a treated plant to agricultural maturity may also be manifested by reduced transpiration or increased carbohydrate deposition or protein content.

It is to be understood that the regulation of corn plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with the novel aspects of the present invention, the N-substituted isocyanoacylamides have been found to be effective in stimulating the growth of corn plants.

The table below summarizes the results of tests conducted to determine the corn growth regulatory activity of the N-substituted isocyanoacylamides as well as the activity of α-isocyanoacylamide. Such tests were conducted as follows.

Vegetative corn plants are grown in the greenhouse and treated with a formulation of the active ingredient when the fifth true leaf is emerging from the whorl of the corn plant. Said formulation is made up of the active ingredient dissolved in water or acetone in the appropriate amount for application at the desired test rate. When the eighth true leaf emerges from the whorl of the corn plant, the plants are harvested and observed for phytotoxic effects, morphological responses and dry weight accumulation. Comparisons were then made with untreated control plants.

| Compound | Rate lb/acre (kilo/hectare) | Dry Weight % of Control |
|---|---|---|
| 7 | 2.5 | 71 |
|   | 0.5 | 72 |
|   | 0.1 | 96 |
| 1 | 2.5 | 90 |
|   | 0.5 | 119 |
|   | 0.1 | 100 |
| 4 | 2.5 | 106 |
|   | 0.5 | 102 |
|   | 0.1 | 98 |
| 5 | 2.5 | 104 |
|   | 0.5 | 98 |
|   | 0.1 | 97 |
| 6 | 2.5 | 108 |
|   | 0.5 | 98 |

-continued

| Compound | Rate lb/acre (kilo/hectare) | Dry Weight % of Control |
|---|---|---|
|    | 0.1 | 94 |
| 10 | 2.5 | 110 |
|    | 0.5 | 104 |
|    | 0.1 | 92 |

The table above illustrates that the compounds of Formula II have been effective in stimulating the growth of corn. By applying said compounds to corn, it is possible therefore to raise a greater amount of forage corn. Furthermore, it has been found that the compounds of the present invention are useful in increasing the yield of corn plants. For example, when N-benzyl-2-isocyanoacetamide was applied to corn, yield increases were obtained especially at the lower rates. The table below summarizes such results.

| Rate mg/plant | Application days after emergence | | |
|---|---|---|---|
|  | 17 days (kg/h) | 29 days (kg/h) | 56 days (kg/h) |
| 0 | 6551.7 | 7672.0 | 7095.7 |
| 1.5 | 7474.4 | 8971.2 | 7667.1 |
| 3.0 | 5196.4 | 8319.3 | 7458.1 |
| 6.0 | 6352.1 | 7532.9 | 6499.1 |

In practicing the methods of this invention, the active ingredients can be used alone or in combination with a material referred to in the art as an adjuvant in liquid or solid form. Formulations are prepared by admixing the active ingredient with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The formulations usually contain from about 0.01 to about 99 percent by weight of active ingredient.

Typically finely-divided solid carriers and inert solid extenders which can be used with the active ingredients include, for example, the talcs, natural and synthetic clays (e.g. kaolinites and attapulgite), pumice, silica, synthetic calcium and magnesium silicates, diatomaceous earth, quartz, Fuller's earth, salt, sulfur, powdered cork, powdered wood, ground corn cobs, walnut flour, chalk, tobacco dust, charcoal, volcanic ash, cottonseed hulls, wheat flour, soybean flour, tripoli and the like. Typical liquid diluents include for example: petroleum fractions such as kerosene, hexane, xylene, benzene, Diesel oil, toluene, acetone, ethylene dichloride, Stoddard solvent, alcohols such as propanol, glycols and the like.

Such formulations, particularly liquids and wettable particles, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein.

Specific surface-active agents which can be used in the formulations of this invention are set out, for example, in Searle U.S. Pat. Nos. 2,426,417; Todd 2,655,447; Jones 2,412,510 and Lenher 2,139,276. In general, less than 50 parts by weight of the surface-active agent is present per 100 parts by weight of formulation.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenyl) and polyoxyethylene derivatives of the mono-higher fatty esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Wettable powder formulations usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total formulation. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely divided particles. The resulting concentrated aqueous suspension is characterized by its extremely small particle size, so that when diluted and sprayed coverage is very uniform.

Dusts are dense finely divided particulate formulations which are intended for application to the soil in dry form. Dusts are characterized by their free-flowing and rapid settling properties so that they are not readily wind-borne to areas where they are of no value. Dusts contain primarily an active ingredient and a dense, free-flowing finely divided particulate extender. However, their performance is sometimes aided by the inclusion of a wetting agent such as those listed hereinbefore under wettable powder compositions and convenience in manufacture frequently demands the inclusion of an inert, absorptive grinding aid. Suitable classes of grinding aids are natural clays, diatomaceous earth and synthetic minerals derived from silica and silicate. Preferred grinding aids include attapulgite clay, diatomaceous silica, synthetic fine silica and synthetic calcium and magnesium silicates.

The inert finely divided solid extender for the dusts can be either of vegetable or mineral origin. The solid extenders are characterized by possessing relatively low surface areas and are poor in liquid absorption. Suitable inert solid extenders for dusts include micaceous talcs, pryophyllite, dense kaolin clays, ground calcium phosphate rock and phyllite, and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Emulsifiable oil formulations are usually solutions of active ingredient in water-immiscible or partially water-immiscible solvents together with a surface-active agent. Suitable solvents for the active ingredient of this invention include hydrocarbons and water-immiscible ethers, esters or ketones. Suitable surface-active agents are anionic, cationic and non-ionic such as alkyl aryl polyethoxy alcohols, polyethylene sorbitol or sorbitan fatty acid esters, polyethylene glycol fatty esters, fatty alkyllol amide condensates, amine salts of fatty alcohol sulfates together with long chain alcohols and oil soluble petroleum sulfonates or mixtures thereof. The emulsifiable oil formulations generally contain from about 5 to 95 parts active ingredient, about 1 to 50 parts surface-active agent and about 4 to 94 parts solvent, all parts being by weight based on the total weight of the emulsifiable oil.

Granules are physically stable particulate formulations comprising active ingredient adhering to or distributed through a basic matrix of an inert, finely divided particulate extender. In order to aid leaching of the active ingredient from the particulate, a surface-active agent such as those listed hereinbefore under wettable powders can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely divided clays such as kaolin clays, hydrated attapulgite or bentonitic clays. These extenders are sprayed or blended with the active ingredient to form the herbicidal formulations.

The mineral particles which are used in the formulations usually have a size range of 10 to 100 mesh, but preferably such that a large majority of the particles have from 14 to 60 mesh with the optimum size being from 20 to 40 mesh. Clay having substantially all particles between 14 and 80 mesh and at least about 80 percent between 20 and 40 mesh is particularly preferred for use in the formulations. The term "mesh" as used herein means U.S. Sieve Series.

The granular formulations generally contain from about 5 parts to about 30 parts by weight of active ingredient per 100 parts by weight of clay and 0 to about 5 parts by weight of surface-active agent per 100 parts by weight of particulate clay. The preferred granular formulations contain from about 10 parts to about 25 parts by weight of active ingredient per 100 parts by weight of clay.

When operating in accordance with the present invention, effective amounts of the active ingredient to elicit the desired response are applied to the plant. Generally, herbicidal responses may be obtained at rates of about one pound and up to 25 or more pounds per acre.

To regulate the growth of corn plants, it is preferred that lower rates ranging from 0.01 to 2.5 pounds per acre be utilized.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

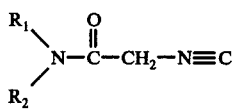

wherein $R_1$ is selected from the group consisting of phenyl and phenyl substituted by one or more halogen or alkyl substituents, said alkyl substituents having up to four carbon atoms, inclusive, benzyl and benzyl substituted on the benzene ring by two halogen or two alkyl substituents, said alkyl substituents having up to four carbon atoms, inclusive; and $R_2$ is selected from the group consisting of hydrogen and alkyl having up to four carbon atoms, inclusive.

2. A compound according to claim 1 wherein $R_1$ is benzyl.

3. A compound according to claim 2 wherein $R_2$ is hydrogen.

4. A method for regulating the growth of corn plants which comprises applying to said corn plants a plant growth regulating effective non-lethal amount of a compound having the formula

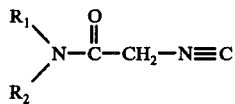

wherein $R_1$ is selected from the group consisting of phenyl, phenyl substituted by one or more halogen or alkyl substituents, said alkyl substituents having up to four carbon atoms, inclusive, benzyl and benzyl substituted on the benzene ring by two halogen or two alkyl substituents, said alkyl substituents having up to four carbon atoms, inclusive; and $R_2$ is selected from the group consisting of hydrogen and alkyl having up to four carbon atoms, inclusive.

5. A method according to claim 4 wherein $R_1$ is benzyl.

6. A method according to claim 5 wherein $R_2$ is hydrogen.

7. A composition for regulating the growth of plants which comprises an adjuvant and a plant growth regulating effective amount of a compound having the formula

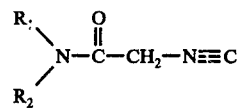

wherein $R_1$ is selected from the group consisting of phenyl, phenyl substituted by one or more halogen or alkyl substituents, said alkyl substituents having up to four carbon atoms, inclusive, benzyl and benzyl substituted on the benzene ring by two halogen or two alkyl substituents, said alkyl substituents having up to four carbon atoms, inclusive; and $R_2$ is selected from the group consisting of hydrogen and alkyl having up to four carbon atoms, inclusive.

8. A composition according to claim 7 wherein $R_1$ is benzyl.

9. A composition according to claim 8 wherein $R_2$ is hydrogen.

10. A method for inhibiting the growth of broadleaf plants which comprises applying to said plants a herbicidally effective amount of a compound having the formula

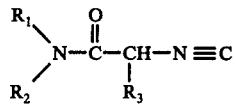

wherein $R_1$ is selected from the group consisting of hydrogen, alkyl having up to four carbon atoms, inclusive, phenyl, phenyl substituted by one or more halogen or alkyl substituents, said alkyl substituents having up to four carbon atoms, inclusive, benzyl and benzyl substituted on the benzene ring by two halogen or two alkyl substituents, said alkyl substituents having up to four carbon atoms, inclusive; $R_2$ and $R_3$ are independently selected from the group consisting of hydrogen and alkyl having up to four carbon atoms, inclusive; provided that when $R_1$ is phenyl, $R_2$ cannot be hydrogen.

11. A method according to claim 10 wherein said compound is α-isocyanoacetamide.

* * * * *